US00PP36604P2

(12) United States Plant Patent
van Dijk

(10) Patent No.: US PP36,604 P2
(45) Date of Patent: Apr. 15, 2025

(54) ***ANTHURIUM* PLANT NAMED 'AN2964275'**

(50) Latin Name: *Anthurium andreanum*
Varietal Denomination: AN2964275

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/791,413

(22) Filed: Jul. 31, 2024

(51) Int. Cl.
*A01H 5/02* (2018.01)
*A01H 6/10* (2018.01)

(52) U.S. Cl.
USPC ..... Plt./365
CPC ..... *A01H 6/10* (2018.05)

(58) Field of Classification Search
USPC ..... Plt./365
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Anthurium* plant named 'AN2964275', characterized by its upright to outwardly arching and uniform plant habit; freely clumping growth habit; bushy and dense plants; narrowly cordate dark green-colored leaves; freely flowering habit; inflorescences that are positioned within to slightly above the foliar plane on strong and mostly upright scapes; broadly cordate white-colored spathes and light orangish yellow-colored spadices; and durable spathes that impart good inflorescence longevity.

2 Drawing Sheets

Figure 1:
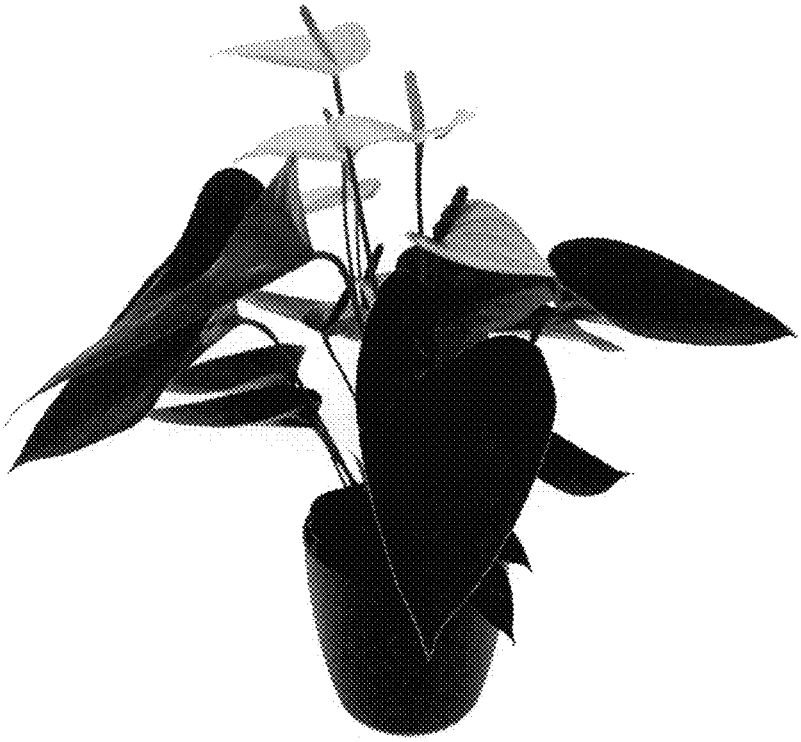

Botanical designation: *Anthurium andreanum.*
Cultivar denomination: 'AN2964275'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B.V. of Bleiswijk, The Netherlands on Nov. 22, 2023, application number 2023/2439. Foreign priority is not claimed to this application.

BACKGROUND OF THE INVENTION

The present invention relates to a new and distinct cultivar of *Anthurium* plant, botanically known as *Anthurium andreanum* and hereinafter referred to by the name 'AN2964275'.

The new *Anthurium* plant is a product of a controlled breeding program conducted by the Inventor in Bleiswijk, The Netherlands. The objective of the breeding program is to create new medium-sized and freely-clumping *Anthurium* plants with attractive and durable white-colored spathes.

The new *Anthurium* plant originated from a cross-pollination made by the Inventor in April, 2013 in Bleiswijk, The Netherlands of *Anthurium andreanum* 'Anthdatam', disclosed in U.S. Plant Pat. No. 27,699, as the female, or seed, parent with a proprietary selection of *Anthurium andreanum* identified as code number 05-012207-0006, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in December, 2014.

Asexual reproduction of the new *Anthurium* plant by in vitro meristem propagation in a controlled environment in Bleiswijk, The Netherlands since August, 2016 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2964275'. These characteristics in combination distinguish 'AN2964275' as a new and distinct *Anthurium* plant:

1. Upright to outwardly arching and uniform plant habit.
2. Freely clumping growth habit; bushy and dense plants.
3. Narrowly cordate dark green-colored leaves.
4. Freely flowering habit.
5. Inflorescences that are positioned within to slightly above the foliar plane on strong and mostly upright scapes.
6. Broadly cordate white-colored spathes and light orangish yellow-colored spadices.
7. Durable spathes that impart good inflorescence longevity.

Plants of the new *Anthurium* differ primarily from plants of the female parent, 'Anthdatam', in the following characteristics:

1. Plants of the new *Anthurium* are more freely clumping than plants of 'Anthdatam'.

2. Spathes of plants of the new *Anthurium* are white in color whereas spathes of plants of 'Anthdatam' are pink in color.
3. Spadices of plants of the new *Anthurium* are light orangish yellow in color whereas spadices of plants of 'Anthdatam' are red purple and orange in color.

Plants of the new *Anthurium* differ primarily from plants of the male parent selection in the following characteristics:

1. Leaves of plants of the new *Anthurium* are not as broad as leaves of plants of the male parent selection.
2. Inflorescences of plants of the new *Anthurium* are held within to slightly above the foliar plane whereas inflorescences of plants of the male parent selection are held way above the foliar plane.
3. Spathes of plants of the new *Anthurium* are flatter than and not as concave as spathes of plants of the male parent selection.

Plants of the new *Anthurium* can also be compared to plants of *Anthurium andreanum* 'Anthdomaq', not patented. In side-by-side comparisons, plants of the new *Anthurium* differ primarily from plants of 'Anthdomaq' in the following characteristics:

1. Spadices of plants of the new *Anthurium* are longer than spadices of plants of 'Anthdomaq'.
2. Spadices of plants of the new *Anthurium* are not as tapering as spadices of plants of 'Anthdomaq'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2964275' grown in a container.

Figure 2:
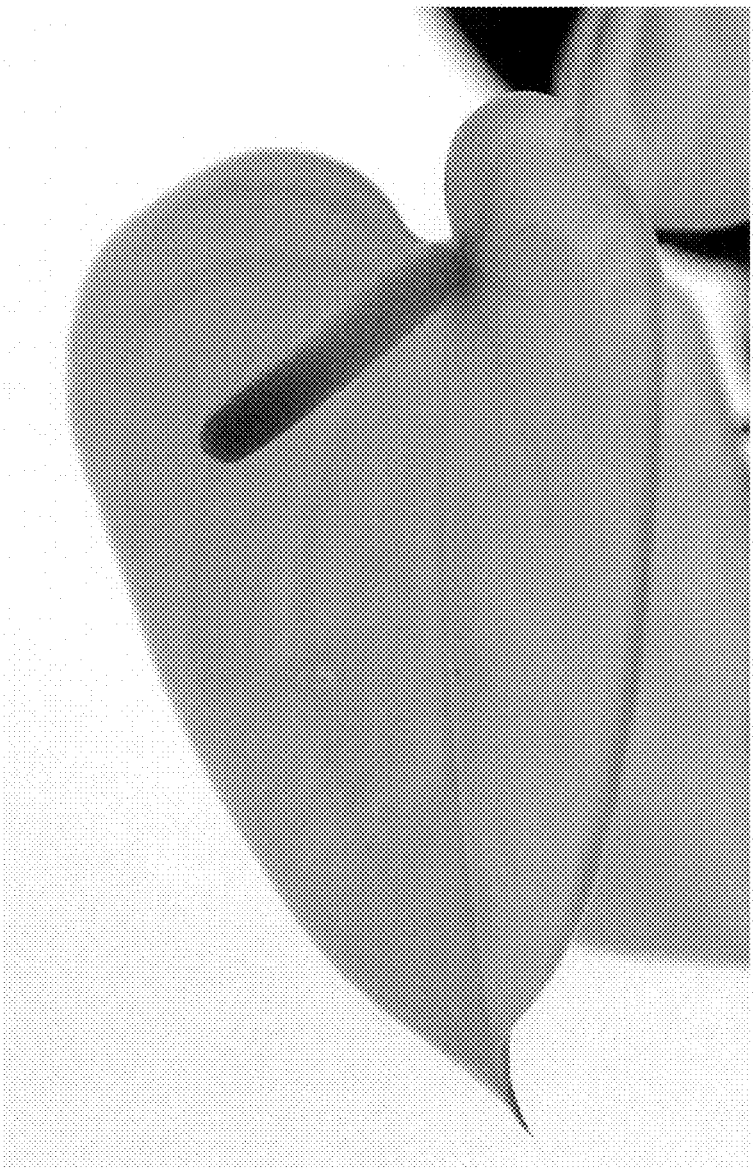

The photograph on the second sheet (FIG. 2) is a close-up view of a typical inflorescence of 'AN2964275'.

DETAILED BOTANICAL DESCRIPTION

The aforementioned photographs and following observations and measurements describe plants grown in 12-cm containers during the late winter in a glass-covered greenhouse in Bleiswijk, The Netherlands. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were ten months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2964275'.

Parentage:

*Female, or seed, parent.*—*Anthurium andreanum* 'Anthdatam', disclosed in U.S. Plant Pat. No. 27,699.

*Male, or pollen, parent.*—Proprietary selection of *Anthurium andreanum* identified as code number 05-012207-0006, not patented.

Propagation:

*Type.*—By in vitro meristem propagation.

*Time to initiate roots, summer and winter.*—About two weeks at temperatures about 19° C. to 22.5° C.

*Time to produce a rooted young plant, summer and winter.*—About six to eight weeks at temperatures about 19° C. to 22.5° C.

*Root description.*—Medium in thickness, fibrous; typically creamy white in color, actual color of the roots is dependent on substrate composition, water quality, fertilizer type and formulation, substrate temperature and physiological age of roots.

*Rooting habit.*—Freely branching, medium density.

Plant description:

*Plant shape.*—Medium-sized, upright to outwardly arching and uniform plant habit; overall shape, roughly broadly obovate to close to spherical.

*Growth habit.*—Freely clumping habit with about six clumps developing per plant imparting a bushy and dense appearance; moderately vigorous growth habit and moderate growth rate.

*Plant height, from soil level to top of leaf plane.*—About 26.9 cm.

*Plant height, from soil level to top of inflorescences.*—About 35.2 cm.

*Plant diameter or spread.*—About 43.1 cm.

Leaf description:

*Arrangement.*—Alternate; simple; about three leaves per clump.

*Length.*—About 16.5 cm.

*Width.*—About 9.8 cm.

*Shape.*—Narrowly cordate.

*Apex.*—Apiculate with a mucronate tip.

*Base.*—Cordate to truncate; basal lobes free.

*Margin.*—Entire; flat to slightly and coarsely undulate.

*Texture and luster, upper and lower surfaces.*—Smooth, glabrous; moderately leathery; glossy.

*Venation pattern.*—Pinnate.

*Color.*—Developing leaves, upper surface: Close to 143A. Developing leaves, lower surface: Close to a blend of 144A and 146B. Fully expanded leaves, upper surface: Close to a blend of NN137A and 139A; narrow marginal edges, close to 143C; venation, close to 137B. Fully expanded leaves, lower surface: Close to 144A; venation, close to N144C.

*Petioles.*—Length: About 16.9 cm. Diameter: Distally, about 3 mm; proximally, about 4.5 mm. Strength: Strong. Texture and luster, upper and lower surfaces: Smooth, glabrous; slightly glossy. Color, upper and lower surfaces: Close to a blend of 144A and 144B. Geniculum length: About 2.1 cm. Geniculum diameter: About 4 mm by 5.5 mm. Geniculum texture, upper and lower surfaces: Smooth, glabrous. Geniculum color, upper surface: Close to 144A. Geniculum color, lower surface: Close to 146C. Wing length: About 2.3 cm. Wing diameter: About 5 mm. Wing color: Close to 144A; towards the margins, close to 145A and 145B.

Inflorescence description:

*Inflorescence arrangement and flowering habit.*—Spathes with spadices held within and slightly above the foliar plane on strong and erect scapes; flowering structures arise from leaf axils; freely and continuous flowering year-round in controlled temperature greenhouses in The Netherlands; typically about ten developing and developed inflorescences per plant at one time; inflorescence development commences about 2.5 to 3.5 months after planting.

*Inflorescence longevity*.—Depending on temperature, spathes maintain good substance for about two months on the plant; inflorescences persistent.

*Fragrance*.—None detected.

*Spathes*.—Length: About 9.1 cm. Width: About 7.7 cm. Shape: Broadly cordate; typically flat to slightly concave. Apex: Broadly apiculate to abruptly acute with a mucronate tip. Base: Cordate. Margin: Entire; slightly and coarsely undulate. Aspect: About 80° from the scape axis. Texture and luster, upper and lower surfaces: Smooth, glabrous; moderately leathery; not rugose; somewhat glossy. Color: When developing, front surface: Close to NN155B; at the apex, close to 145D. When developing, rear surface: Close to NN155B; at the apex, close to 145D; towards the base, close to 157A. Fully developed, front surface: Close to 155C; at the apex, close to 145D; towards the base, tinged with close to 145D; venation, close to 145A and 145B; with subsequent development, colors becoming closer to 150D, at the apex, close to 144C, towards the center, tinged with close to 145C, towards the base, close to 144A and 144B with venation, close to 143B. Fully developed, rear surface: Close to 155C; at the apex, close to 145C; towards the base, tinged with close to 145D; venation, close to 145A and 145B; with subsequent development, colors becoming closer to 157A and 157B, at the apex, close to 146B, towards the base, close to 145A and 146D with venation, close to 143A.

*Spadices*.—Length: About 3.8 cm. Diameter: About 8 mm. Shape: Columnar, slightly tapering towards the apex; apex, obtuse; base, obtuse; in cross-section, rounded. Aspect: About 65° from the spathe axis and about 12.5° from the scape axis. Color: Immature: Close to 160B and 160C; towards the apex, close to 144C. Mature: Close to 158B; towards the apex, close to 159B. Flowers: Type: Hermaphroditic. Quantity per spadix: Numerous, about 160. Height: Less than 0.5 mm. Diameter: About 2.5 mm. Shape: Roughly square. Anther color: Close to 159B. Pollen amount: Moderate. Pollen color: Close to 155D. Stigma color: Close to 161A.

*Scapes*.—Length: About 24.7 cm. Diameter: About 3 mm. Strength: Strong. Aspect: About 15° from vertical. Color: Close to 144A.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2964275' as herein illustrated and described.

* * * * *